United States Patent
Fridkin et al.

(10) Patent No.: US 7,182,945 B2
(45) Date of Patent: Feb. 27, 2007

(54) ANTI-INFLAMMATORY PEPTIDES DERIVED FROM C-REACTIVE PROTEIN

(75) Inventors: Matityahu Fridkin, Rehovot (IL); Eran Yavin, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 10/373,794

(22) Filed: Feb. 27, 2003

(65) Prior Publication Data

US 2003/0152564 A1 Aug. 14, 2003

Related U.S. Application Data

(62) Division of application No. 09/446,868, filed as application No. PCT/IL98/00302 on Jun. 29, 1998, now Pat. No. 6,528,618.

(30) Foreign Application Priority Data

Jun. 29, 1997 (IL) ..................... 121191

(51) Int. Cl.
A61K 38/43 (2006.01)
A61K 38/00 (2006.01)
C12N 9/50 (2006.01)
A01N 37/18 (2006.01)
C07K 1/00 (2006.01)

(52) U.S. Cl. ............... 424/94.1; 435/212; 435/218; 435/219; 514/2; 514/15; 530/300; 530/326; 530/328

(58) Field of Classification Search .............. 424/94.1; 435/212, 218, 219; 514/2, 15; 530/300, 530/326, 328

See application file for complete search history.

(56) References Cited

OTHER PUBLICATIONS

Wright et al. Am J Respir Med. 2003;2(3):211-9 (ABSTRACT).*
van den Berg. Clin Exp Rheumatol. Sep.☐Oct. 2002;20(5 Suppl 27):S21-5 (ABSTRACT).*
Leff AR, "Future Directions in Asthma Therapy: Is a Cure Possible?", *Chest* 111(2Supp):61S-68S (1997).
Odeh M, "New insights into the pathogenesis and treatment of rheumatoid arthritis", *Clin Immunol Immunopathol* 83(2):103-116 (1997).
Stehbens et al, "Proteinase imbalance versus biomechanical stress in pulmonary emphysema", *Exp Mol Pathol* 69(1):46-62 (2000).
Shephard et al, "Peptides generated from C-reactive protein by a neutrophil membrane protease. Amino acid sequence and effects of peptides on neutrophil oxidative metabolsm and chemotaxis", *J Immunol* 145(5):1469-1476 (1990).
Shephard et al, "Characterization of neutrophil-mediated degradation of human C-reactive protein and identification of the protease", *Clin Exp Immunol* 87(3):509-513 (1992).
Shephard et al, "C-reactive protein (CRP) peptides inactivate enolase in human neutrophils leading to depletion of intracellular ATP and inhibition of superoxide generation", *Immunology* ;76(1):79-85 (1992).
West et al, "Gene therapy for pulmonary diseases", *Chest* 119(2):613-617 (2001).
Yavin et al, "Proteolysis of human C-reactive protein by neutrophil-derived lysosomal enzymes generated peptides which modulate neutrophil function: Implications to the anti-inflammatory mechanism", *Letters in Pept Sci* 2:7-16 (1995).
Yavin et al, "Synthetic peptides derived from the sequence of human C-reactive protein inhibit the enzymatic activities of human leukocyte elastase and human leukocyte cathespin G", *Int J Pept Protein Res* 48(5):465-76 (1996).
Yavin EA, "Binding pockets on the surface of human leukocyte elastase and human leukocyte cathepsin G. Implications to the design of inhibitors derived from human C-reactive protein", *Biomed Pept Proteins Nucleic Acids* 2(3):71-8 (1996-97).
Yavin EA, "Inhibition of the HLE and Cathespin G by Extended Peptides and Subunits Derived from Human C-reactive Protein", *Letters n Pept Sci* 4(3):157-166 (1997).
Yavin et al, "Peptides derived from human C-reactive protein inhibit the enzymatic activities of human leukocyte elastase and cathepsin G: use of overlapping peptide sequences to identify a unique inhibitor", *J Pept Res* 51(4):282-289 (1998).

* cited by examiner

*Primary Examiner*—Tekchand Saidha
*Assistant Examiner*—Christian L. Fronda
(74) *Attorney, Agent, or Firm*—Browdy and Neimark, PLLC (57) ABSTRACT

A peptide corresponding to positions 62–71 of the sequence of human C-reactive protein (CRP) of the formula: $Glu_{62}$-Ile-Leu-Ile-Phe-Trp-Ser-Lys-Asp-$Ile_{71}$ and modifications thereof obtained by substitution, deletion, or addition of amino acids, amidation of the C-terminal or acylation of the N-terminal, are capable of inhibiting in vitro the enzymatic activity of human Leukocyte Elastase (hLE) and/or of human Cathepsin G (hCG) and can be used for the treatment of chronic inflammation conditions such as rheumatoid arthritis, pulmonary emphysema, cystic fibrosis, bronchitis, asthma and some acute respiratory distress syndrome.

1 Claim, 3 Drawing Sheets pGlu-Thr-Asp-Met-Ser-Arg-Lys-Ala-Phe-Val-Phe-Pro-Lys-Glu-Ser-  15
Asp-Thr-Ser-Tyr-Val-Ser-Leu-Lys-Ala-Pro-Leu-Thr-Lys-Pro-Leu-  30
Lys-Ala-Phe-Thr-Val-Cys-Leu-His-Phe-Tyr-Thr-Glu-Leu-Ser-Ser-  45
Thr-Arg-Gly-Tyr-Ser-Ile-Phe-Ser-Tyr-Ala-Thr-Lys-Arg-Gln-Asp-  60
Asn-Glu-Ile-Leu-Ile-Phe-Trp-Ser-Lys-Asp-Ile-Gly-Tyr-Ser-Phe-  75
Thr-Val-Gly-Gly-Ser-Glu-Ile-Leu-Phe-Glu-Val-Pro-Glu-Val-Thr-  90
Val-Ala-Pro-Val-His-Ile-Cys-Thr-Ser-Trp-Glu-Ser-Ala-Ser-Gly-  105
Ile-Val-Glu-Phe-Trp-Val-Asp-Gly-Lys-Pro-Arg-Val-Arg-Lys-Ser-  120
Leu-Lys-Lys-Gly-Tyr-Thr-Val-Gly-Ala-Glu-Ala-Ser-Ile-Ile-Leu-  135
Gly-Gln-Glu-Gln-Asp-Ser-Phe-Gly-Gly-Asn-Phe-Glu-Gly-Ser-Gln-  150
Ser-Leu-Val-Gly-Asp-Ile-Gly-Asn-Val-Asn-Met-Trp-Asp-Phe-Val-  165
Leu-Ser-Pro-Asp-Glu-Ile-Asn-Thr-Ile-Tyr-Leu-Gly-Gly-Pro-Phe-  180
Ser-Pro-Asn-Val-Leu-Asn-Trp-Arg-Ala-Leu-Lys-Tyr-Glu-Val-Gln-  195
Gly-Glu-Val-Phe-Thr-Lys-Pro-Gln-Leu-Trp-Pro-OH  206

Figure 1

CRP      Cys36-LHFYTELSSTRGYSIFSYATKRQDNEILIFWSKDIGYSFTVGGSEILFEVPEVTVAPVHI-Cys97

Peptide 1    LHFYTELSSTRGYSI
Peptide 2        ELSSTRGYSIFSYAT
Peptide 3            RGYSIFSYATKRQDN
Peptide 4                FSYATKRQDNEILIF
Peptide 5                    KRQDNEILIFWSKDI
Peptide 6                        EILIFWSKDIGYSFT
Peptide 7                            WSKDIGYSFTVGGSE
Peptide 8                                GYSFTVGGSEILFEV
Peptide 9                                    VGGSEILFEVPEVTV
Peptide 10                                       ILFEVPEVTVAPVHI

ANTI-INFLAMMATORY PEPTIDES DERIVED FROM C-REACTIVE PROTEIN

The present application is a division of U.S. application Ser. No. 09/446,868, filed Mar. 28, 2000, now U.S. Pat. No. 6,528,618, which application was the national stage under 35 U.S.C. §371 of PCT/IL98/00302, filed Jun. 29, 1998.

FIELD OF THE INVENTION

The present invention relates to synthetic peptides derived from the primary sequence of the acute phase reactant C-reactive protein (CRP) (SEQ ID NO:1), more particularly to a peptide corresponding to positions 62–71 of CRP and derivatives thereof, which peptides inhibit in vitro the enzymatic activities of human leukocyte elastase (hLE) and/or human leukocyte cathepsin G (hCG), two potent serine proteases associated with tissue damage occurring in the course of several chronic inflammatory conditions. The invention further relates to anti-inflammatory pharmaceutical compositions comprising said CRP-derived peptides.

Abbreviations:

The following abbreviations will be used throughout the specification:

CRP, C-reactive protein; hLE, human leukocyte elastase; hCG, human leukocyte cathepsin G; MeOSuc-AAPV-NA, methoxysuccinyl-Ala-Ala-Pro-Val-nitroanilide (SEQ ID NO:2), Suc-AAPF-NA, succinyl-Ala-Ala-Pro-Phe-nitroanilide (SEQ ID NO:3).

BACKGROUND OF THE INVENTION

C-reactive protein (CRP) is a plasma protein classified as a major acute phase reactant due to its dramatic accumulation in the blood stream during the inflammatory response. Within a relatively short period (24–48 hr) following tissue injury or certain traumatic events, the CRP blood concentration may rise 1000-fold over the normal level to as high as 1 mg/ml (Ballue and Kushner, 1992).

CRP consists of five identical sub-units that contain each 206 amino acids bridged by a single disulfide bond and that aggregate non-covalently into a cyclic pentamer termed pentraxin. The precise biochemical function of CRP as a whole entity is still obscure. CRP was shown to bind to specific receptors on human neutrophils ($K_d$~$5\times10^{-8}$ M), monocytes ($K_d$~$10^{-7}$ M), and other inflammatory-related cells in vitro (Ballue and Kushner, 1992).

In the laboratories of the present inventors and their collaborators it was found that following binding to neutrophils, CRP is subsequently degraded by a membrane-associated neutral serine protease, which has been characterized (Shephard et al., 1992), and by lysosomal-derived enzymes to yield various low molecular weight peptides. Several of these peptides were identified, synthesized, and shown to be potent anti-inflammatory agents inhibiting neutrophil phagocytosis, degranulation, and superoxide ion ($O_2^-$) generation (Shephard et al., 1990; Yavin et al., 1995). Superoxide ion is the parent compound of several destructive mediators that are believed to play a central role in inflammation-associated tissue injury (Ballue and Kushner, 1992).

The most prominent of the peptides disclosed by Shephard et al., 1990, and Yavin et al., 1995, were derived from within the primary sequence of CRP (SEQ ID NO:1) as follows: $Asp_{70}$-Ile-Gly-Tyr-$Ser_{74}$, $Lys_{201}$-Pro-Gln-Leu-Trp-$Pro_{206}$, $Leu_{83}$-Phe-Glu-Val-Pro-Glu-Val-$Thr_{90}$, $Val_{77}$-Gly-Gly-Ser-Glu-$Ile_{82}$ (Shepard et al., 1990) and $Asn_{160}$-Met-Trp-Asp-Phe-$Val_{165}$, $Gln_{203}$-Leu-Trp-$Pro_{206}$, $Ser_{18}$-Tyr-Val-Ser-Leu-$Lys_{23}$ (Yavin et al., 1995). These peptides were shown by the authors to inhibit various neutrophilic functions, indicating that they may be capable of regulating superoxide ion production by neutrophils in vivo during the acute phase response as part of a complex protective mechanism. However, as disclosed in the PCT Publication No. WO 97/28182 of the same applicants, several of these peptides lack hLE inhibitory capability.

Human leukocyte elastase (hLE) and human leukocyte cathepsin G (hCG) are the two major potent neutral serine proteases found in the azurophilic granules of neutrophils which are involved in the intracellular digestion of proteins and play an important role in phagocytosis and host defense against invading organisms. In the extracellular environment, hLE is capable of degrading various connective tissue proteins including highly cross-linked elastin whereas hCG is very effective in degrading proteoglycans and collagens and has been shown to augment the elastolytic capability of hLE (Groutas, 1987).

The release of enzymes into the extracellular medium by activated neutrophils is normally controlled by several potent inhibitors. The most specific natural inhibitors, $\alpha_1$-protease inhibitor ($\alpha_1$-PI) and $\alpha$-antichymotrypsin (ACT), are directed against hLE and hCG, respectively (Groutas, 1987). Imbalances in the levels of tissue proteases such as hLE and hCG, and their inhibitors, allow excess hLE and hCG to attack connective tissue, and are implicated in the severe and permanent tissue damage associated with pulmonary emphysema (Groutas, 1987), rheumatoid arthritis (Gallin et al., 1988), cystic fibrosis (Jackson et al., 1984) and several other inflammatory conditions. Major research efforts have been dedicated to develop potent inhibitors of hLE and hCG based on a wide variety of low molecular weight organic compounds (Edwards and Bernstein, 1994) such as 3,3-dialkylazetidin-2-ones, proposed as orally active β-lactam inhibitors of hLE (Finke et al., 1995).

Figure 1:
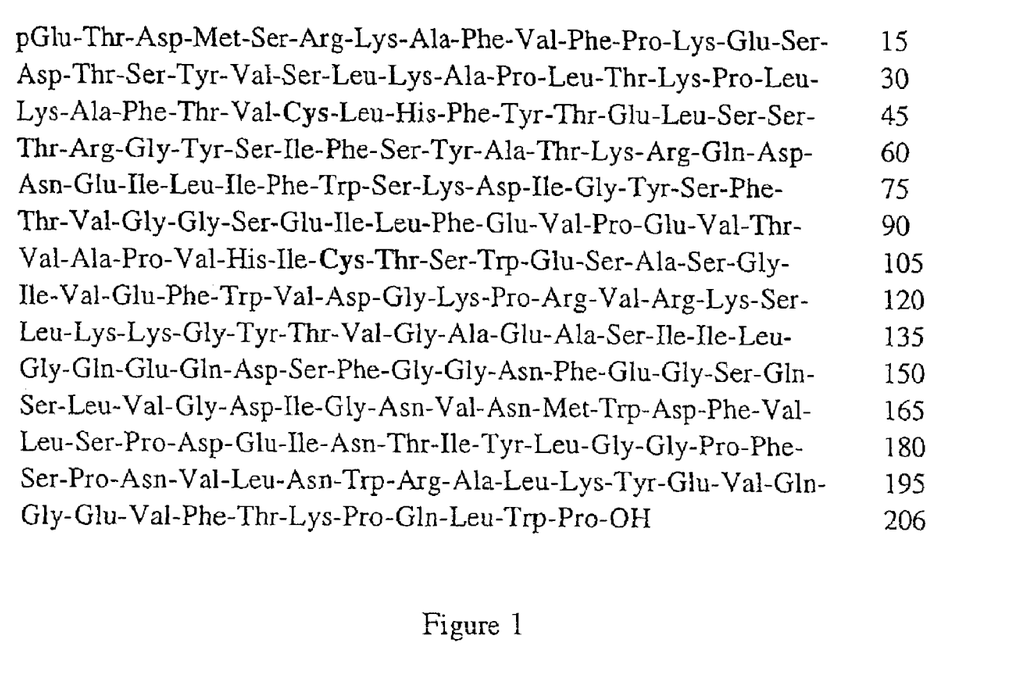
FIG. 1 depicts the primary sequence of human C-reactive protein (CRP) (SEQ ID NO:1). The two cystein residues (at positions 36 and 97) which comprise the single disulfide bond within each subunit are marked in bold letters.

CRP as a whole protein was reported to have no inhibitory effect on hLE (Vachino et al., 1988). In contrast, a specific region within the primary seguence of CRE containing the core peptide $Val_{89}$-Thr-Val-Ala-Pro-Val-His-$Ile_{96}$ of SEQ ID NO:1 was shown to inhibit in vitro the enzymatic activities of hLE and hCG to a larger extent than peptides of similar chain lengths corresponding to the active sites of their natural inhibitors (PCT Publication No. WO 97/28182; Yavin et al., 1996). Novel biologically active CRP-derived peptides, i.e. peptides capable of inhibiting in vitro the enzymatic activity of hLE and/or of hCG, previously concealed within the inner hydrophobic disulfide loop which spans CRP36-97 in each subunit (see FIG. 1), have been found in accordance with the present invention to significantly inhibit the enzymatic activities of hLE and hCG enzymes.

SUMMARY OF THE INVENTION

The present invention relates to a synthetic CRP-derived peptide capable of inhibiting in vitro the enzymatic activity of human leukocyte elastase (hLE) and/or of human cathepsin G (hCG), said peptide being selected from:

(i) a core peptide corresponding to positions 62–71 of the sequence of human C-reactive protein (CRP) of the formula:

$Glu_{62}$-Ile-Leu-Ile-Phe-Trp-Ser-Lys-Asp-$Ile_{71}$ or peptides resulting from modification thereof characterized by:

(ii) substitution of $Glu_{62}$ by Asp or by a non-amino acid negatively charged residue derived from succinic, glutaric or adipic acids;

(iii) substitution of each of the residues $Ile_{63}$, $Leu_{64}$, $Ile_{65}$, $Phe_{66}$ or $Trp_{67}$ by a natural or non-natural hydrophobic amino acid residue;

(iv) deletion of 1 or 2 amino acid residues selected from $Ile_{63}$, $Leu_{64}$, $Ile_{65}$, $Phe_{66}$ and $Trp_{67}$;

(v) substitution of 1–3 amino acid residues selected from $Ile_{63}$, $Leu_{64}$, $Ile_{65}$, $Phe_{66}$ and $Trp_{67}$ by a single non-natural amino acid residue derived from 6-aminocaproic acid;

(vi) substitution of 2–4 amino acid residues selected from $Ile_{63}$, $Leu_{64}$, $Ile_{65}$, $Phe_{66}$ and $Trp_{67}$ by a single non-natural amino acid residue derived from 8-aminocaproic acid, 10-aminodecanoic acid or 12-aminolauric acid;

(vii) substitution of 3–5 amino acid residues selected from $Ile_{63}$, $Leu_{64}$, $Ile_{65}$, $Phe_{66}$ and $Trp_{67}$ by a stretch of identical hydrophobic amino acid residues or by a single non-natural amino acid residue derived from 10-aminodecanoic acid or 12-aminolauric acid;

(viii) substitution of $Ser_{68}$ by a natural or non-natural amino acid residue selected from Thr, Cys, Ala and homoserine;

(ix) substitution of $Lys_{69}$ by a natural or non-natural positively charged or hydrophobic amino acid residue;

(x) substitution of $Asp_{70}$ by a negatively charged or a polar amino acid residue selected from Glu, Asn or Gln;

(xi) substitution of $Ile_{71}$ by a natural or non-natural hydrophobic amino acid residue;

(xii) elongation of a peptide (i) to (xi) by 1–5 non-charged amino acid residues at the N-terminus and/or at the C-terminus;

(xiii) substitution of any amino acid residue in a peptide (i) to (xii) by the corresponding N-alkyl derivative, D-amino acid residue or by another isoster;

(xiv) an amide of the C-terminal of a peptide (i) to (xiii); and (xv) an N-acyl derivative of a peptide (i) to (xiv).

The invention further relates to anti-inflammatory pharmaceutical compositions comprising a CRP-derived peptide of the invention and a pharmaceutically acceptable carrier.

In another aspect, the invention relates to a method of treatment of an inflammatory disorder, e.g. rheumatoid arthritis, pulmonary emphysema, cystic fibrosis, bronchitis, asthma, acute respiratory distress syndrome and other chronic inflammatory tissue destructive conditions, which comprises administering to a patient in need thereof an effective amount of a CRP-derived peptide according to the invention.

DETAILED DESCRIPTION OF THE INVENTION

The present invention provides a series of synthetic peptides derived from positions 62–71 of the sequence of CRP and to pharmaceutical compositions comprising them which are anti-inflammatory by inhibiting either hLE or hCG activity, or both. These biologically active peptides according to the invention can be used to inhibit hLE and/or hCG and thereby have utility in controlling tissue damage associated with chronic inflammation.

Figure 2:
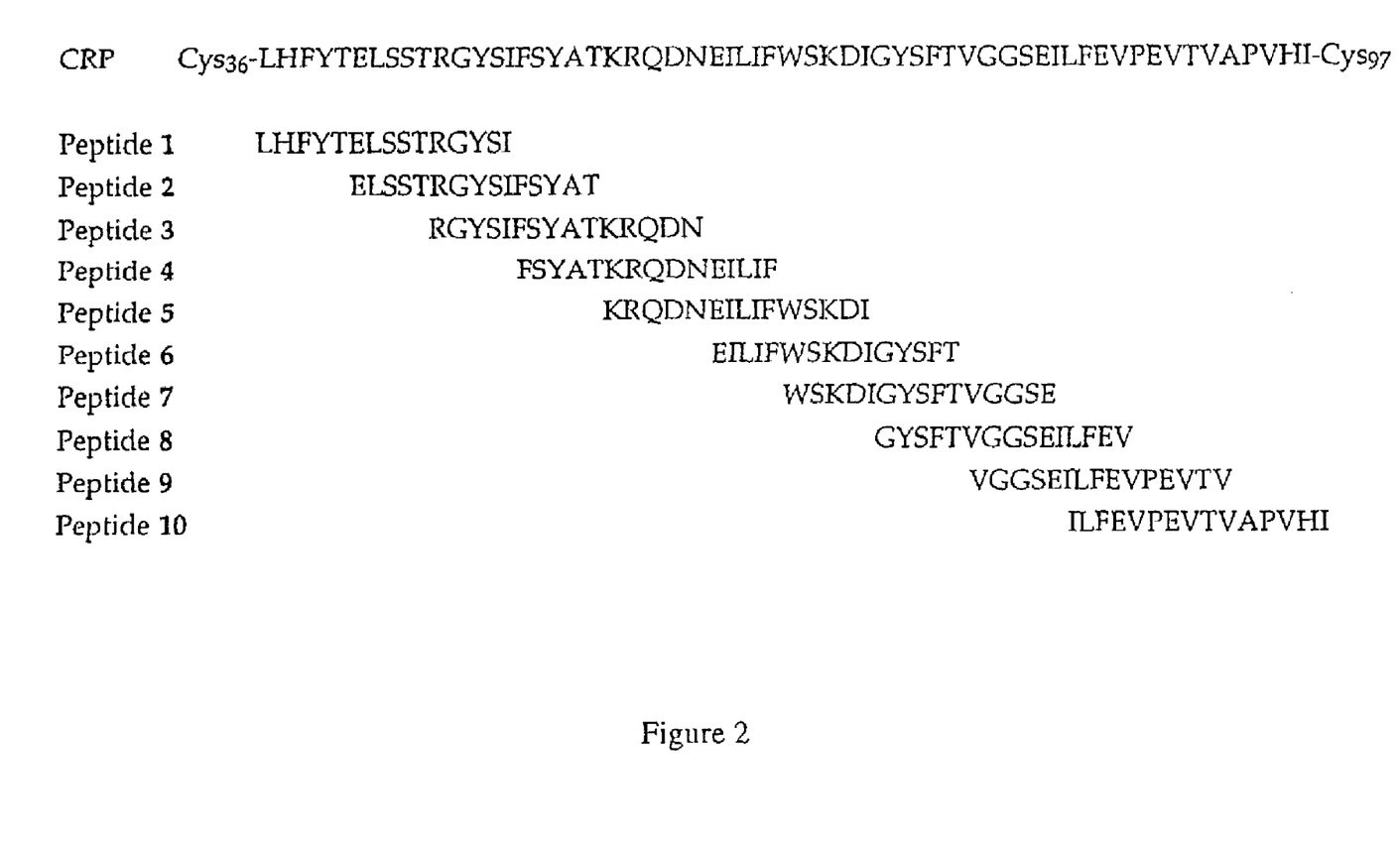
FIG. 2 depicts the sequence alignment of the CRP-derived 15-mer peptides, herein designated peptides 1–10, within the disulfide loop region of the CRP36-97 sequence of SEQ ID NO:1.

The CRP hydrophobic disulfide loop domain contains hydrophobic amino acid stretches concealed within the intact protein and many of the previously described biologically active CRP-derived peptides originate from this region following CRP binding to neutrophils and subsequent proteolysis. A series of overlapping peptides derived from within the CRP's hydrophobic disulfide loop (CRP 36–97), herein designated peptides 1–10, were synthesized according to the invention and are depicted in FIG. 2. Each successive peptide, 15 amino acids in length, overlapped in 10-amino acid sequence with each one of its neighboring peptides. The hLE and hCG inhibitory activities of these peptides were evaluated as shown in Examples 4 and 6 and Table 1 hereinafter.

It was found according to the invention that Peptide 6 corresponding to positions 62–76 of the CRP sequence possesses a unique inhibitory activity towards both hLE and hCG observed at submicromolar concentrations of the peptide. Surprisingly, it was found that this inhibitory activity is two orders of magnitude more potent than the peptides which contain the sequences $Val_{89}$-Thr-Val-Ala-Pro-Val-His-$Ile_{96}$ of SEQ ID NO:1 previously described in PCT Publication No. WO 97/28182 and Yavin et al., 1996.

The unique inhibitory activity of peptide 6 ($CRP_{62-76}$) was further studied by synthesizing and examining the inhibitory effect of analogs and variants thereof in which one or more amino acid residues have been added, deleted or replaced by natural or non-natural amino acid residues (see Table 2, peptides 11–26).

Figure 3:
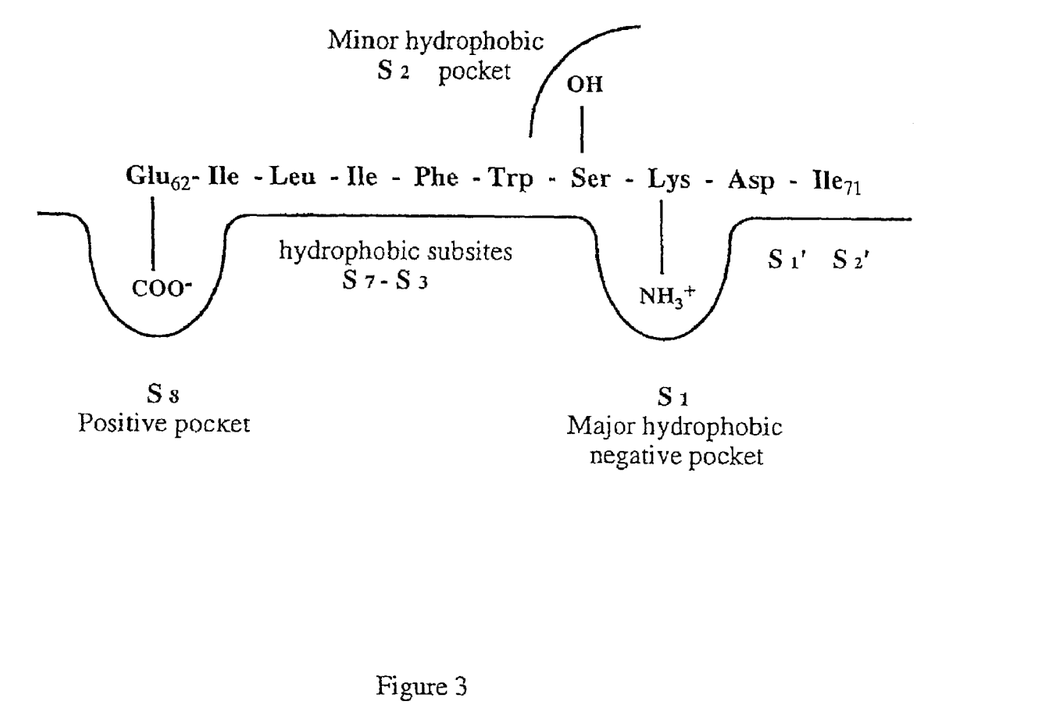
FIG. 3 depicts a schematic representation of hLE's (and possibly hCG's) subsites designated $S_8$–$S_2'$, interacting with a segment of peptide 6 (amino acid residues $Glu_{62}$-$Ile_{71}$ of SEQ ID NO:1). The $S_8$–$S_2'$ notation is used to designate subsites on the surface of the enzyme with respect to the amino acids in the peptide inhibitor ($P_8$–$P_2'$, respectively), and the theoretical cleavage site on the peptide at the $Lys_{69}$-$Asp_{70}$ bond (denoted $P_1$–$P_1'$). The negative side chain of CRP's $Glu_{62}$ is shown to reside within the positive pocket of hLE and the positive side chain of $Lys_{69}$ is shown to reside within the major hydrophobic pocket of hLE which possesses considerable negative charge.

A possible mode of binding of peptide 6 in which the negative charge of $Glu_{62}$ residue interacts with hLE's (and possibly hCG's) positive pocket (Yavin et al., 1997) is depicted schematically in FIG. 3. In such a suggested binding configuration, the $Lys_{69}$ residue of CRP fits into hLE major negative-hydrophobic pocket with the hydrophobic amino acids $Ile_{63}$, $Leu_{64}$, $Ile_{65}$, $Phe_{66}$ and $Trp_{67}$ traversing the space between the two distant pockets and interacting with the enzyme's hydrophobic surface.

Peptide 6 is remarkably resistant to proteolysis, it binds and inhibits both hLE and hCG but is not susceptible to proteolytic inactivation by them. The stability of the peptide bonds in peptide 6 were evaluated by incubating the peptide with hLE and hCG and monitoring proteolysis by reverse-phase HPLC chromatography analysis. Surprisingly, no cleavage products were observed using the degradation conditions as described by Yavin et al., 1996, even after 12 hours of the peptide incubation at 37° C.

In order to determine the significance of the amino acid residues at specific positions with respect to the inhibitory activity of peptide 6, short peptides obtained by deletion of amino acid residues from the N- and/or C-terminus of peptide 6 (see Table 2, peptides 11–16) were carefully studied for their inhibitory effects.

The residue $Glu_{62}$ is the preferred amino acid residue at this position; a dramatic loss in both hLE and hCG inhibitory activities is observed when the N-terminus $Glu_{62}$ is removed (peptide 11) indicating the crucial role this negatively charged residue plays. It can however be replaced by another negatively charged amino acid such as Asp (peptide 18) or by a non-amino acid negatively charged residue such as a residue derived from succinic, glutaric or adipic acids. The negative charge of the substituting residue is important for the inhibitory activity of the peptide, as well as the fitting of the substituting residue into the enzyme's positive pocket.

The hydrophobic amino acid residues $Ile_{63}$ and $Leu_{64}$ are critical in establishing hydrophobic interactions needed for efficient binding. However, the residues $Ile_{63}$, $Leu_{64}$, $Ile_{65}$, $Phe_{66}$ and $Trp_{67}$ of peptide 6 may be interchanged or replaced by natural or non-natural hydrophobic amino acid residues selected from Ala, Val, Leu, Ile, Phe, Trp, Tyr, Nva and Nle. One to five of the amino acid residues of this stretch may be substituted by a stretch of identical amino acid residues as indicated before, e.g. a stretch of 4 or 5 Ala residues, or by a non-natural amino acid residue spacer derived from 6-aminocaproic acid, 8-aminocaproic acid, 10-aminodecanoic acid or 12-aminolauric acid, with the proviso that the overall length of this stretch is not significantly changed. For example, 1–3 amino acid residues may be substituted by a single amino acid residue derived from 6-aminocaproic acid, 2–4 amino acid residues may be substituted by a single amino acid residue derived from 8-aminocaproic acid or 10-aminodecanoic acid, and 3–5 amino acid residues may be substituted by a stretch of 3–5 Ala residues or by a single amino acid residue derived from 10-aminodecanoic acid or 12-aminolauric acid. Minor deletions (up to two amino acid residues) within this hydrophobic stretch are also possible, still allowing the binding of both charges into the respective charged pockets on the surface of both hLE and hCG enzymes (FIG. 3).

The residue $Ser_{68}$ allows flexibility in contrast to proline which was observed at the $S_2$ position of many inhibitors, including the previously described CRP derived core peptide $Val_{89}$-Thr-Val-Ala-Pro-Val-His-$Ile_{96}$ of SEQ ID NO:1 (PCT Publication No. WO 97/28182; Yavin et al., 1996). This residue may be substituted by a similar compact amino acid such as Thr, Cys or Ala, or by a non-natural isoster such as homoserine.

Peptide 6 is less sensitive to removal of amino acids at the C-terminus. Removing the first three amino acids at end (peptide 13) results in diminished inhibitory activity towards both enzymes, yet less than the loss of activity observed with the removal of the single N-terminus amino acid residue $Glu_{62}$. Furthermore, peptide 6 may tolerate the removal of five C-terminus amino acid residues (peptide 14) and still retain significant inhibitory activity, indicating that the interaction of this part of the peptide with both enzymes is less specific in comparison to the charged amino acids and hydrophobic section ($Ile_{63}$-$Trp_{67}$).

The residue $Lys_{69}$ is the preferred residue at this position, yet it may be replaced by another positively charged amino acid residue such as Arg, His, homolysine, ornithine (Orn) or diaminobutyric acid (DAB) or by an hydrophobic amino acid such as Ala, Val, Leu, Ile, Phe, Nva or Nle. Bulky amino acids such as Phe, Tyr and His are preferred amino acid residues at this position ($P_1$) in hCG inhibitors (Yavin et al., 1997). Modification of $Lys_{69}$ as described above may lead to peptide bond cleavage by both enzymes in which case it is advisable to use D-amino acids at this position.

The $Asp_{70}$ and $Ile_{71}$ residues are important in establishing a strong fit with both hLE's and hCG's surfaces. A negatively charged residue at position $Asp_{70}$ is essential for the peptide inhibitory activity towards hLE and hCG.

The residue $Asp_{70}$ is the preferred residue at this position, yet it may be replaced by a negatively charged or a polar amino acid residue such as Glu, Asn or Gln. Modification of this residue may lead to peptide bond cleavage by both enzymes in which case it is advisable to use D-amino acids or preferably N-alkyl derivatives of the substituting residue.

The residue $Ile_{71}$ is the preferred residue at this position, yet it may be replaced by a large hydrophobic amino acid residue such as Leu, Ile, Phe and Tyr, or by an isoster such as Nva, Nle, homoleucine, homoisoleucine and aminobutyric acid (ABU).

Elongation of peptide 6 by one to five non-charged amino acid residues at the N- and/or C-terminus does not impair its inhibitory activity, but a more extended elongation, for example, by addition of amino acid residues according to the sequence of CRP at both the N- and C-terminus such as in peptide 17, leads to a reduction of inhibitory activity towards both hLE and hCG. This decrease in activity may arise from an unfavorable conformation or folding of the 29-amino acid peptide.

The residues $Gly_{72}$, $Tyr_{73}$, $Ser_{74}$, $Phe_{75}$ and $Thr_{76}$ may be replaced by non-charged amino acid residues and are less critical in establishing potent inhibition.

As a general rule, additional charged amino acids besides in the specific positions of $Glu_{62}$ and $Lys_{69}$ should be avoided such as not to cause a gross misalignment of the peptide inhibitor on the enzyme's surface (see FIG. 3).

Amides ($CO-NH_2$) of the carboxy terminal of the peptides of the invention are also encompassed by the invention and show an inhibitory activity towards hLE and hCG as well as N-acyl derivatives of the N-terminal such as those corresponding to the formula R—X—CO— wherein R is a substituted or unsubstituted hydrocarbyl, preferably alkyl or aryl, and X is a covalent bond, O, NH or NHCO. Examples of acyl radicals are octanoyl, monomethoxysuccinyl, acetylaminocaproyl, adamantyl-NH—CO—, and more preferably, carbobenzoxy (benzyl-O—CO—), naphthyl-NH—CO—, and Fmoc (fluorenylmethyl-O—CO—).

The peptides according to the invention have a hLE $K_i$ lower of about 8.0 μM, preferably 0.1–3.0 μM. Thus, preferred CRP-derived peptides according to the invention are the peptides 6, 13, 18, 20–23 and 25–26.

The peptides of the invention are prepared by standard methods for the synthesis of peptides, for example as set forth in the Examples hereinbelow.

In another aspect, the present invention relates to pharmaceutical compositions comprising a peptide of the invention and a pharmaceutically acceptable carrier. The compositions are prepared by well-accepted methods for preparation of peptide-containing pharmaceutical compositions for administration in a suitable form, e.g. orally, subcutaneously, intranasal, and parenterally including intravenous, intramuscular and intraperitoneally, according to the inflammatory condition to be treated.

In a further aspect, the invention relates to a method of treatment of a chronic inflammatory condition which comprises administering to a patient in need thereof an effective amount of a peptide according to the invention. Examples of such chronic inflammatory conditions are rheumatoid arthritis, pulmonary emphysema, cystic fibrosis, bronchitis, asthma and acute respiratory distress syndrome. The anti-inflammatory peptide is administered and dosed in accordance with good medical practice, taking into consideration the clinical condition of the patient, the site and method of administration, schedule of administration and other factors known to medical practitioners.

The invention will now be illustrated by the following non-limiting examples.

EXAMPLES

Materials and Methods (i) General Solid Phase Peptide Synthesis: Peptides were prepared by conventional solid phase peptide synthesis, with ABIMED AMS-422 automated solid phase multiple peptide synthesizer (Langenfeld, Germany). The Fmoc-strategy (9-fluorenyl-methoxycarbonyl) was used through peptide chain assembly, following the company's commercial protocols. In each reaction vessel, 12.5 µmol of Wang resin was used which contained the first, covalently bound, corresponding N-Fmoc C-terminal amino acid (typical polymer loadings of 0.3–0.7 mmols/g resin were employed). Fmoc deprotection was achieved using duplicate treatments with 20% piperidine in dimethylformamide (DMF), typically for 10–15 min at room temperature, depending on the length of peptide and Fmoc-protected amino acid type, as given by the company's protocols.

Side chain-protecting groups were tert.-butytoxycarbonyl (t.-Boc) for Lys, diaminobutyric-acid (DAB), and Trp; trityl (Trt) for Asn, Cys, Gln, His, and (D)-His; tert.-butyl-ester (O-t-But) for Asp and Glu; tert.-butyl-ether (t-But) for Ser, Thr, and Tyr.

Coupling was achieved, as a rule, using two successive reactions with 50 µmol (4 eqv.) of corresponding N-Fmoc protected amino acid, 50 µmol (4 eqv.) of PyBOP reagent (benzotriazole-1-oxytris-pyrrolidino-phosphonium-hexafluoro-phosphate), and 100 µmol (µeqv.) of 4-methyl-morpholine (NMM), all dissolved in DMF, typically for 20–45 min at room temperature, depending on the length of peptide and amino acid derivative type, as given by the company's protocols.

Cleavage of the peptide from the polymer was achieved by reacting the resin with trifluoroacetic acid/$H_2O$/triethylsilane (TFA/$H_2O$/TES; 90/5/5; v/v) for 1.5 to 2 hours at room temperature. In the cleavage of peptides which contained Arg and Trp (peptide 5), the cleavage mixture was composed of TFA/$H_2O$/ethanediol/thioanisol/cresol (80/5/5/5/5-v/v). The respective solutions containing the crude unprotected peptides were then cooled down to 4° C., precipitated with ice-cold di-tert.-butylether (DTBE) and centrifuged for 15 min, 3000 RPM at 4° C. The pellet was washed and centrifuged 3 times with DTBE, dissolved in 30% acetonitrile in $H_2O$, and lyophilized.

All protected amino acids, coupling reagents, and polymers were obtained from Nova Biochemicals (Laufelfingen, Switzerland). Synthesis-grade solvents were obtained from Labscan (Dublin, Ireland).

(ii) Reversed-phase high performance liquid chromatography (RP-HPLC): Synthetic peptides were purified by using a prepacked LiChroCart RP-18 column (250×10 mm, 7 µm bead size), employing a binary gradient formed from 0.1% TFA in $H_2O$ (solution A) and 0.1% TFA with 25% $H_2O$ in acetonitrile (solution B), eluted at t=0 min B=5% t=5 min B=5% t=60 min B=70% (flow-rate 5 mL/min). Analytical RP-HPLC was performed using a prepacked Lichrospher-100 RP-18 column (4×250 mm, 5 µm bead size) using the same buffer system (flow-rate 0.8 mL/min). All peptide separations were performed using a Spectra-Physics SP8800 liquid chromatography system equipped with an Applied Biosystems 757 variable wave-length absorbance detector. The column effluents were monitored by UV absorbance at 220 mm, and chromatograms were recorded on a Chrome-Jet integrator. Following HPLC purification, the lyophilized peptides (generally>90% pure for crude samples after synthesis as described below) were purified to>97%. All solvents and HPLC columns were obtained from Merck (Darmstadt, Germany).

(iii) Amino acid composition analysis: Purified peptide solutions were roto-evaporated (~40 µg of peptide in 40 µL solution with 5 µg of norleucine as an un-natural amino acid internal standard), hydrolyzed in 6 N HCl at 110° C. for 22 hours under vacuum and analyzed with a Dionex amino acid analyzer. This quantification was used as a basis for determination of the total yield of peptide. Several of the peptides synthesized were analyzed by Electrospray mass-spectrometry which confirmed their expected molecular weights.

(iv) Isolation of hLE and hCG: The isolation of neutrophilic enzymes was based on the two-step aprotinin-sepharose affinity chromatography and carboxymethyl-cellulose (CMC) ion exchange chromatography (Heck et al., 1985). Neutrophils (1.4 billion) were isolated from whole blood obtained from a single healthy laboratory donor by dextran sedimentation and Ficoll/hypaque gradient centrifugations as described elsewhere (Metcalf et al., 1986). The enzymatic activity was assayed with MeOSuc-AAPV-NA for hLE determination and Suc-AAPF-NA for hCG determination (both in 100 mM Hepes buffer, pH 7.4, containing 0.05% of the anionic detergent Brij-35). The activities of the individual enzymatic fractions were 100% free from cross-contamination. The step-wise elution profile on the CMC column with a long 0.45 M NaCl elution step (20 column volumes) afforded the effective separation between the two enzymes. The fractions containing hLE and hCG were dialyzed each against 0.1% pyridinium acetate, pH 5.3, divided into 20 aliquots, lyophilized, and stored at −20° C. until use. By the initial rates of reactions and the known values of $K_{cat}$ (hLE=54 µM, hCG=2900 µM) and $K_m$ (hLE=13.3 sec.$^{-1}$, hCG=3.1 sec.$^{-1}$), the amount of enzyme was estimated to be approximately 15 µg/aliquot for hLE and 12 µg/aliquot for hCG, such values being confirmed by active site titration with $α_1$-protease inhibitor and α-anti-chymotrypsin.

(v) Inhibition experiments with hLE: Peptides were dissolved in 100 mM Hepes buffer pH 7.4 containing 0.1% Brij-35 with 10% DMSO to yield 300 µM solutions, which were used to make further dilutions with the same buffer, and 80 µL aliquots were added in duplicates to 96-well plates. The substrate, 600 µM MeOSuc-AAPV-NA in the same buffer with 5% DMSO, was added to each well in addition to the blank wells, and the plate was placed in the plate reader equilibrated to 37 C (Dynateck MR-6000). Lyophilized aliquots of hLE were dissolved in 1600 µL of 100 mM Hepes buffer without DMSO, and 80 µL of the enzyme solution was added to the peptides and substrate to initiate the reaction. The kinetics program read the plate at 405 nm every 2 min for 20 min (with a 3 sec shaking period between readings), and plotted the results as well as the average of each duplicate. The final volume was 240 µL containing: 5% DMSO, 1–100 µM of peptide, 200 µM substrate, and 0.75 µg (~25 picomol) enzyme.

(vi) Inhibition experiments with hCG: Similar conditions to hLE inhibition experiments were used except the substrate: 80 µL of 1.80 mM Suc-AAPF-NA. The enzyme was dissolved in 800 µL buffer, and the reaction was monitored every 6 min for 1 hour. The final volume was 240 μL containing: 5% DMSO, 1–100 μM peptide, 600 μM substrate, and 1.2 μg enzyme (about 40 picomol).

(vii) Degradation profiles of peptides by RP-HPLC: Several active peptide inhibitors were dissolved in calcium- and magnesium-free phosphate-buffered saline (PBS), 125 μg/250 μL, mixed with 0.25 aliquots of hLE or hCG in 250 μL PBS and incubated at 37° C. Periodically (up to 12 hrs), 100 μL samples were removed from the reaction vessel. The samples were diluted with 150 μL of 0.1% TFA, frozen with liquid nitrogen, and stored at –20° C. prior to HPLC analysis.

(viii) Calculations: For hLE, V is determined by fitting a linear equation to the first 6 time-points (10 min) of the kinetics data using the least squares method. Without exception, all $R^2$ factors were>0.998. Several inhibitor concentration in duplicates and two control wells were used to fit a linear equation to graphs of $V_o/V_i-1$ vs. [I] for each inhibitor using the least squares method (8 data points for each inhibitor). From calculating the error in the slope of the equation, the relative error for $K_i$ was deduced:

$$K_i = \{slope*(1+[S]/K_m)\}^{-1} \text{ because } K_i = [I]*\{(1+[S]/K_m)*(V_o/V_i-1)\}^{-1}.$$

For hCG, V is determined by fitting a quadratic equation to the total kinetic data (60 min), using the least squares method and calculating V at t=0. Without exception, all $R^2$ factors were>0.996. Two inhibitor concentrations in duplicate and two control wells were used for each inhibitor, and in a similar fashion to hLE, $K_i$ was deduced (6 data points for each inhibitor).

Example 1

Synthesis of Peptides 1–26

In the synthesis of peptide 6, $Glu_{62}$-Ile-Leu-Ile-Phe-Trp-Ser-Lys-Asp-Ile-Gly-Tyr-Ser-Phe-$Thr_{76}$, the standard Fmoc protocol was used as follows:

| Peptide elongation cycle: | |
| --- | --- |
| Step 1. DMF wash | x6 |
| Step 2. Deprotection: 20% piperidine in DMF | x2 |
| Step 3. DMF wash | x6 |
| Step 4. Derivative coupling. | x2 |
| At the end of synthesis: | |
| Step 1. DMF wash | x6 |
| Step 2. Deprotection: 20% piperidine in DMF | x2 |
| Step 3. DMF wash | x6 |
| Step 4. $CH_2Cl_2$ wash | x6 |

Deprotection, coupling and wash times and volumes, were calculated by the ABIMED computer program. The resulting lyophilized crude peptide was purified by preparative HPLC to yield approx. 15 mg of lyophilized peptide (white powder), above 98% pure, as determined by its analytical RP-HPLC. Amino acid analysis confirmed the expected sequence, purity, and yield of purified peptide (see Table 3).

Additional peptides 5, 11, 13, 14, 17, 18, 20–23, 25–26 of the invention and comparison peptides 1–5, 7, 10, 12, 15, 16, 19 and 24 were synthesized in a similar manner using the appropriate amino acid residues.

The sequence of the peptides 1–26 and their inhibition constants ($K_i$) of human hLE and human hCG are shown in Tables 1 and 2. The amino acid analysis of the same peptides are shown in Table 3.

Example 2

Synthesis of C-terminus Amides of the Peptides

C-terminus amidated peptides (peptide-$NH_2$) are prepared according to previously described procedures (PCT Publication No. WO 97/28182; Yavin et al., 1996): The standard resin is replaced with rink amide solid support [4-2'(4'-dimethoxyphenyl-Fmoc-aminomethyl)-phenoxy -resin] which does not contain the first amino acid. Peptide synthesis is followed in an identical fashion as described in Example 1 above, and upon cleavage from the polymer, the carboxy terminus amidated form of the peptide is obtained.

TABLE 1

Amino acid sequence of CRP-derived peptides 1–10 and their inhibition constants (Ki) of hLE and hCG.

| Peptide | Sequence | hLE Ki [μM] | hCG Ki [μM] |
| --- | --- | --- | --- |
| 1 $CRP_{37-51}$ | Leu-His-Phe-Tyr-Thr-Glu-Leu-Ser-Ser-Thr-Arg-Gly-Tyr-Ser-Ile | w.i. | n.s.i. |
| 2 $CRP_{42-56}$ | Glu-Leu-Ser-Ser-Thr-Arg-Gly-Tyr-Ser-Ile-Phe-Ser-Tyr-Ala-Thr | n.s.i. | n.s.i. |
| 3 $CRP_{47-61}$ | Arg-Gly-Tyr-Ser-Ile-Phe-Ser-Tyr-Ala-Thr-Lys-Arg-Gln-Asp-Asn | n.s.i. | n.s.i. |
| 4 $CRP_{52-66}$ | Phe-Ser-Tyr-Ala-Thr-Lys-Arg-Gln-Asp-Asn-Glu-Ile-Leu-Ile-Phe | n.s.i. | w.i. |
| 5 $CRP_{57-71}$ | Lys-Arg-Gln-Asp-Asn-Glu-Ile-Leu-Ile-Phe-Trp-Ser-Lys-Asp-Ile | 85 ± 10 | 180 ± 25 |
| 6 $CRP_{62-76}$ | Glu-Ile-Leu-Ile-Phe-Trp-Ser-Lys-Asp-Ile-Gly-Tyr-Ser-Phe-Thr | 0.18 ± 0.03 | 0.25 ± 0.05 |
| 7 $CRP_{67-81}$ | Trp-Ser-Lys-Asp-Ile-Gly-Tyr-Ser-Phe-Thr-Val-Gly-Gly-Ser-Glu | n.s.i. | w.i. |
| 8 $CRP_{72-86}$ | Gly-Tyr-Ser-Phe-Thr-Val-Gly-Gly-Ser-Glu-Ile-Leu-Phe-Glu-Val | n.s.i | w.i. |
| 9 $CRP_{77-91}$ | Val-Gly-Gly-Ser-Glu-Ile-Leu-Phe-Glu-Val-Pro-Glu-Val-Thr-Val | n.s.i. | w.i. |
| 10 $CRP_{82-96}$ | Ile-Leu-Phe-Glu-Val-Pro-Glu-Val-Thr-Val-Ala-Pro-Val-His-Ile | 55 ± 5 | 150 ± 15 |

Each one of peptides 1–10 corresponds to a 15-mer within the stretch of CRP36-96. Subscript numbers in column 1 denote the residue positions of each peptide within the primary sequence of CRP (SEQ ID NO:1). w.i.; weak inhibition (>200 μM). n.s.i.; no significant inhibition.

TABLE 2

Amino acid sequence of CRP-derived peptides and analogs 6, 11–30 and their inhibition constants (Ki) of hLE and hCG.

| Peptide | Sequence | hLE Ki [μM] | hCG Ki [μM] |
| --- | --- | --- | --- |
| 6 $CRP_{62-76}$ | Glu-Ile-Leu-Ile-Phe-Trp-Ser-Lys-Asp-Ile-Gly-Tyr-Ser-Phe-Thr | 0.18 ± 0.03 | 0.25 ± 0.05 |

TABLE 2-continued

Amino acid sequence of CRP-derived peptides and analogs 6, 11–30 and their inhibition constants (Ki) of hLE and hCG.

| Peptide | Sequence | hLE Ki [μM] | hCG Ki [μM] |
|---|---|---|---|
| 11 CRP$_{63-76}$ | Ile-Leu-Ile-Phe-Trp-Ser-Lys-Asp-Ile-Gly-Tyr-Ser-Phe-Thr | 4.5 ± 0.5 | 15 ± 4 |
| 12 CRP$_{65-76}$ | Ile-Phe-Trp-Ser-Lys-Asp-Ile-Gly-Tyr-Ser-Phe-Thr | n.s.i. | n.s.i. |
| 13 CRP$_{62-73}$ | Glu-Ile-Leu-Ile-Phe-Trp-Ser-Lys-Asp-Ile-Gly-Tyr | 1.1 ± 0.2 | 4.0 ± 0.6 |
| 14 CRP$_{62-71}$ | Glu-Ile-Leu-Ile-Phe-Trp-Ser-Lys-Asp-Ile | 6.7 ± 1.0 | 6.0 ± 1.0 |
| 15 CRP$_{62-69}$ | Glu-Ile-Leu-Ile-Phe-Trp-Ser-Lys | n.s.i. | n.s.i. |
| 16 CRP$_{68-74}$ | Ser-Lys-Asp-Ile-Gly-Tyr-Ser | n.s.i. | n.s.i. |
| 17 CRP$_{55-83}$ | Ala-Thr-Lys-Arg-Gln-Asp-Asn-Glu-Ile-Leu-Ile-Phe-Trp-Ser-Lys-Asp-Ile-Gly-Tyr-Ser-Phe-Thr-Val-Gly-Gly-Ser-Glu-Ile-Leu | 7.3 ± 1.0 | 5.5 ± 1.0 |
| 18 | Asp-Ile-Leu-Ile-Phe-Trp-Ser-Lys-Asp-Ile-Gly-Tyr-Ser-Phe-Thr | 2.2 ± 0.4 | 2.6 ± 0.5 |
| 19 | Glu-Ile-Leu-Ile-Phe-Trp-Ser-Pro-Lys-Asp-Ile-Gly-Tyr-Ser-Phe-Thr | n.s.i. | 30 ± 5 |
| 20 | Glu-Ile-Leu-Ile-Phe-Trp-Ser-Orn-Asp-Ile-Gly-Tyr-Ser-Phe-Thr | 0.25 ± 0.10 | 0.25 ± 0.05 |
| 21 | Glu-Ile-Leu-Ile-Phe-Trp-Ser-DAB-Asp-Ile-Gly-Tyr-Ser-Phe-Thr | 0.20 ± 0.05 | 0.85 ± 0.35 |
| 22 | Glu-Ile-Leu-Ile-Phe-Trp-Ser-Lys-Ala-Ile-Gly-Tyr-Ser-Phe-Thr | 3.0 ± 0.6 | 5.5 ± 1.5 |
| 23 | Glu-Ile-Leu-Ile-Phe-Trp-Ser-Lys-Glu-Ile-Gly-Tyr-Ser-Phe-Thr | 0.55 ± 0.15 | 0.85 ± 0.25 |
| 24 | Thr-Phe-Ser-Tyr-Gly-Ile-Asp-Lys-Ser-Trp-Phe-Ile-Leu-Ile-Glu (reverse sequence) | 10 ± 2 | — |
| 25 | Glu-Ile-Leu-Ile-Phe-Trp-Ser-Ala-Asp-Ile | 3.0 ± 0.5 | — |
| 26 | Glu-Ile-Leu-Ile-Phe-Trp-Ser-Val-Asp-Ile | 2.0 ± 0.5 | — |

Peptides 11–26 are analogs and variants of peptide 6 (CRP$_{62-76}$). Subscript numbers in column 1 denote the residue positions of the peptide within the primary sequence of CRP (SEQ ID NO:1). Peptides 18–26 correspond to SEQ ID NOs:4–12, respectively. Substituted amino acids are underlined. w.i.; weak inhibition (>200 μM). n.s.i.; no significant inhibition. ——; undetermined. Error margins were calculated for each inhibitor as described in Material and Methods section viii.

TABLE 3

The amino acid analysis ratios and HPLC retention times (R.T.) of peptides 1–26. The theoretical values are without exception those obtained by rounding off each value to the closest integer.
*In peptides 20 and 21, (L)-ornithine (Orn) and 1,4-(L)-diaminobutyricacid (DAB) respectively.

| Pep. | Asp/n | Glu/n | Ser | His | Gly | Thr | Ala | Arg | Tyr | Val | Ile | Phe | Leu | Lys* | Pro | R.T. |
|---|---|---|---|---|---|---|---|---|---|---|---|---|---|---|---|---|
| 1 | — | 0.95 | 2.80 | 1.00 | 1.05 | 1.85 | — | 1.00 | 1.90 | — | 0.95 | 0.95 | 1.90 | — | — | 25.8 |
| 2 | — | 0.95 | 4.00 | — | 1.05 | 1.95 | 1.00 | 1.00 | 2.00 | — | 1.00 | 1.00 | 1.00 | — | — | 25.8 |
| 3 | 1.95 | 1.00 | 1.95 | — | 1.00 | 0.90 | 1.00 | 2.00 | 1.95 | — | 1.00 | 1.00 | — | 1.05 | — | 22.7 |
| 4 | 2.00 | 2.00 | 1.00 | — | — | 0.95 | 1.00 | 1.00 | 0.95 | — | 2.00 | 2.00 | 1.00 | 1.10 | — | 28.7 |
| 5 | 2.95 | 1.90 | 1.05 | — | — | — | — | 1.00 | — | — | 3.20 | 1.00 | 1.00 | 2.15 | — | 29.8 |
| 6 | 1.00 | 1.05 | 2.00 | — | 1.00 | 0.95 | — | — | 0.95 | — | 3.10 | 2.00 | 1.00 | 0.95 | — | 31.9 |
| 7 | 1.05 | 1.00 | 3.00 | — | 3.25 | 1.00 | — | — | 1.00 | 1.00 | 1.00 | 1.00 | — | 1.10 | — | 23.4 |
| 8 | — | 2.00 | 2.00 | — | 3.10 | 0.95 | — | — | 1.00 | 2.00 | 1.00 | 2.00 | 1.00 | — | — | 30.8 |
| 9 | — | 3.00 | 1.00 | — | 2.10 | 0.95 | — | — | — | 4.00 | 1.00 | 1.00 | 1.00 | — | 1.00 | 29.2 |
| 10 | — | 2.00 | — | 1.10 | — | 0.95 | 1.05 | — | — | 3.95 | 2.00 | 1.00 | 1.00 | — | 1.95 | 30.9 |
| 11 | 1.05 | — | 2.05 | — | 1.05 | 0.95 | — | — | 0.95 | — | 3.05 | 2.00 | 1.00 | 0.95 | — | 32.6 |
| 12 | 1.00 | — | 2.00 | — | 1.05 | 1.00 | — | — | 0.95 | — | 2.15 | 2.05 | — | 1.00 | — | 28.5 |
| 13 | 1.00 | 1.00 | 1.05 | — | 1.00 | — | — | — | 0.95 | — | 3.20 | 1.00 | 1.00 | — | — | 32.0 |
| 14 | 1.15 | 0.85 | 1.10 | — | — | — | — | — | — | — | 3.30 | 1.00 | 1.00 | 1.00 | — | 31.1 |
| 15 | — | 1.00 | 1.00 | — | — | — | — | — | — | — | 2.15 | 1.00 | 1.00 | 1.00 | — | 30.2 |
| 16 | 1.00 | — | 2.00 | — | 1.10 | — | — | — | 1.00 | — | 1.00 | — | — | 1.15 | — | 13.5 |
| 17 | 2.95 | 2.95 | 2.80 | — | 3.25 | 1.85 | 1.00 | 1.00 | 0.90 | 1.00 | 4.10 | 2.00 | 2.00 | 2.20 | — | 32.4 |
| 18 | 2.05 | — | 2.00 | — | 1.05 | 0.95 | — | — | 1.00 | — | 3.00 | 2.10 | 1.00 | 1.05 | — | 33.1 |
| 19 | 1.05 | 0.95 | 0.90 | — | 1.10 | 1.00 | — | — | 1.00 | — | 3.00 | 2.21 | 1.00 | 1.15 | 1.00 | 33.6 |
| 20 | 1.10 | 1.00 | 1.95 | — | 1.05 | 1.00 | — | — | 1.00 | — | 3.00 | 2.10 | 1.05 | 1.05* | — | 32.6 |
| 21 | 1.05 | 1.00 | 1.90 | — | 1.05 | 0.95 | — | — | 0.95 | — | 3.00 | 1.95 | 1.00 | 1.00* | — | 32.7 |
| 22 | — | 1.00 | 1.90 | — | 1.10 | 1.00 | 1.05 | — | 1.05 | — | 3.00 | 2.05 | 1.00 | 1.05 | — | 33.4 |

TABLE 3-continued

The amino acid analysis ratios and HPLC retention times (R.T.) of peptides 1–26. The theoretical values are without exception those obtained by rounding off each value to the closest integer.
*In peptides 20 and 21, (L)-ornithine (Orn) and 1,4-(L)-diaminobutyricacid (DAB) respectively.

| Pep. | Asp/n | Glu/n | Ser | His | Gly | Thr | Ala | Arg | Tyr | Val | Ile | Phe | Leu | Lys* | Pro | R.T. |
|---|---|---|---|---|---|---|---|---|---|---|---|---|---|---|---|---|
| 23 | — | 2.05 | 1.80 | — | 1.10 | 1.00 | — | — | 1.05 | — | 3.00 | 2.00 | 0.95 | 1.05 | — | 32.8 |
| 24 | 1.05 | 1.00 | 2.00 | — | 0.95 | 0.95 | — | — | 1.00 | — | 3.05 | 2.05 | 0.95 | 1.00 | — | 32.2 |
| 25 | 1.05 | 0.85 | 1.00 | — | — | — | 1.00 | — | — | — | 3.15 | 1.05 | 1.00 | — | — | 32.7 |
| 26 | 1.00 | 0.95 | 1.05 | — | — | — | — | — | — | 1.05 | 3.05 | 1.00 | 0.95 | — | — | 32.9 |

Example 3

Synthesis of N-acyl Peptides

N-terminus acylated peptides (R—CO-peptide) are prepared according to previously described procedures (PCT Publication No. WO 97/28182; Yavin et al., 1996): Several organic compounds which contain a free carboxylic acid moiety are used for coupling to the exposed N-terminus of the peptides as the final step of solid phase peptide synthesis prior to peptide-polymer cleavage and deprotection. Examples of such organic compounds are: mono-methyl-succinic-acid, $CH_3OCO(CH_2)_2COOH$, $CH_3(CH_2)_6COOH$ and N-acetyl-amino-caproic acid. PyBOP and NMM coupling is used as described in the Materials and Methods section (i) followed by extensive flushing with N-methyl-pyrrolidone (NMP) and $CH_2Cl_2$.

Example 4

Synthesis of N-terminus Fmoc Peptides

The synthesis of Fmoc peptides is carried out as in Example 1 above except that the final step of Fmoc deprotection is omitted. The Fmoc moiety is stable under peptide-polymer cleavage and side-chain deprotection conditions, thus yielding N-terminus Fmoc-peptides as the end products of the synthesis.

Example 5

In Vitro Inhibition of hLE by the Peptides of the Invention

The hLE inhibitory capability of CRP-derived peptides was evaluated by inhibiting the enzymatic cleavage of MeOSuc-AAPV-NA as described in Materials and Methods (section v). The results are shown in Tables 1 and 2.

As shown in Table 1, the CRP-derived peptide 6 is extremely potent in inhibiting hLE. Total inhibition was observed at concentrations above 50 μM and only by diluting the peptide to the 1–10 μM range, the determination of a $K_i$ value for peptide 6 was made possible.

In contrast, from the other 9 peptides of the series 1–10, derived from overlapping sequences within CRP36-97, only peptides 5 and 10 displayed hLE inhibitory activity in the 50–100 μM range, still two orders of magnitude less potent than peptide 6, while peptides 1–4 and 7–9 were inactive.

Peptides 11–16 shown in Table 2 represent short peptides in which 1–7 amino acid residues from the N- and/or C-terminus of peptide 6 were deleted. The most dramatic effect due to removal of a single amino acid residue was observed when the $Glu_{62}$ residue was removed (peptide 11) resulting in around 20 fold decrease in hLE inhibition. Further removal of the two subsequent amino acid residues $Ile_{63}$ and $Leu_{64}$ totally abolished the inhibitory activity (peptide 12).

Removal of amino acid residues at the C-terminus of peptide 6 was less effective in impairing the peptide inhibitory activity. Removal of the first three amino acids at the C-terminus of peptide 6 (peptide 13) resulted in diminished hLE inhibitory activity, albeit less than the loss of activity observed with the removal of the N-terminus residue $Glu_{62}$. Furthermore, peptide 14, that lacks the five C-terminus amino acid residues of peptide 6, still retains significant inhibitory activity.

Peptide 15, that further lacks the $Asp_{70}$ and $Ile_{71}$ residues, showed a total loss of inhibitory activity. As expected, peptide 16, missing both the C-terminus and the critical N-terminus amino acid residues, was also totally inactive.

Peptide 17, which is a 29-mer peptide ($CRP_{55-83}$) containing the amino acid sequence of peptide 6 and additional amino acid residues according to the CRP sequence at its N- and C-terminus, has a reduced inhibitory activity which may result from an unfavorable conformation or folding of this longer peptide. In this respect, a comparison between peptide 5 and peptide 14 confirms that the additional sequence of amino acids $Lys_{57}$-Arg-Gln-Asp-$Asn_{61}$ added to the N-terminus of peptide 14 drastically lowered the inhibitory capability by more than one order of magnitude.

In order to evaluate the significance of a specific amino acid residue at a particular position with respect to the inhibitory activity of peptide 6, the substitution analogs peptides 18–26 were examined. Peptide 18, in which $Glu_{62}$ was substituted by the smaller negatively charged amino acid Asp, shows a 10-fold lower inhibitory activity comparing to peptide 6, supporting the notion that the steric arrangement of the negatively charged residue at this position is of major importance.

Peptide 19, in which $Ser_{68}$ was replaced by Pro, showed a dramatic two orders of magnitude loss of inhibitory activity (see Table 2). This loss may be due to the bend introduced by the Pro amino acid residue in the middle of the peptide preventing a good fit between the adjacent $Lys_{69}$ and the $S_1$ pocket (FIG. 3).

Peptides 20 and 21 in which $Lys_{69}$ was substituted, respectively, by either ornithine or DAB, retained the same level of inhibitory activity as peptide 6. Both ornithine and DAB are small positively charged residues fitting in the replaced $Lys_{69}$ position without interfering with the peptide structure and interaction with the inhibited enzyme.

Substitution of $Asp_{70}$ by another negatively charged amino acid residue Glu (peptide 23) resulted in a small decrease in inhibitory activity, while substitution at the same position by Ala (peptide 22), a non-charged amino acid residue, resulted in a large decrease in inhibition capacity, stressing the importance of a negative charge at this position.

The reverse sequence of peptide 6 (peptide 24), is 30 fold less active towards hLE inhibition, stressing the importance of the precise binding conformation as depicted in FIG. 3.

In peptides 25 and 26, the Lys$_{69}$ residue was substituted by small hydrophobic amino acids (Ala and Val, respectively) to yield inhibitors which are slightly more potent than peptide 14.

Example 6

In Vitro Inhibition of hCG by the Peptides of the Invention

The hCG inhibitory capability of CRP-derived peptides was evaluated by inhibiting the enzymatic cleavage of Suc-AAPF-NA as described in Materials and Methods (section vi). The results are shown in Tables 1 and 2.

The CRP-derived peptide 6, was shown to be extremely potent in inhibiting hCG. At concentrations above 50 µM, total inhibition was observed. In contrast, from the other 9 peptides of the series 1–10, derived from overlapping sequences within CRP36-97 (FIG. 2), only peptides 5 and 10 displayed hCG inhibitory activity in the 150–200 µM range, 600–800 folds less potent than peptide 6, while peptides 1–4 and 7–9 were inactive.

According to the invention it is shown that modifications of the core peptide 6 examined in peptides 11–23 lead to similar effects on the hCG as well as on the hLE inhibitory activity. The same conclusions drawn for the significance of each amino acid residue at its particular position with respect to the inhibitory activity towards hLE generally apply for the inhibitory activity towards hCG.

Example 7

Evaluation of Peptide 6 Resistance to Proteolysis

Peptide 6 exhibits a remarkably resistance to proteolysis; it binds and inhibits both hLE and hCG but is not susceptible to proteolytic inactivation by them. The stability of the peptide bonds in peptide 6 were evaluated by incubating the peptide with hLE and hCG and monitoring degradation profiles of the peptide by reverse-phase HPLC. Briefly, peptide 6 was dissolved in calcium- and magnesium-free phosphate-buffered saline (PBS), 50 µg/250 µL, mixed with 3 µg of hLE or hCG in 250 µL PBS and incubated at 37° C.

Periodically, after 1,3,8, and 12 hrs incubation, 100 µL samples were removed from the reaction vessel. The samples were diluted with 150 µL of 0.1% TFA, frozen with liquid nitrogen, and stored at −20° C. prior to HPLC analysis. Surprisingly, no cleavage products were observed even after 12 hours of the peptide 6 incubation at 37° C.

REFERENCES

1. Ballue, S. P. & Kushner, I. (1992) C-reactive protein and the acute phase response. *Advances in Internal Medicine,* 37, 313–336.
2. Bode, B., Meyer, E. & Powers, C. J. (1989) Human leukocyte elastase and porcine pancreatic elastase; X-ray crystal structures, mechanism, substrate specifity and mechanism based inhibitors. *Biochemistry,* 28(5), 1951–1963.
3. Edwards, P. D., Bernstein, P. R. (1994) Synthetic inhibitors of Elastase. *Med. Res. Rev.* 14, 127–194 and references cited therein.
4. Finke, P. E. et al., (1995) Orally active β-lactam inhibitors of human leukocyte elastase. 3. Stereospecific synthesis and structure—Activity relationships for 3,3-dialkylazetidin-2-ones. *J. Med. Chem.* 38, 2449–2462.
5. Gallin, J. I., Goldstein, I. M. & Snyderman, R. (1988) Inflammation. Chapter 41, Pathogenesis of rheumatoid arthritis: A disorder associated with dysfunctional immunoregulation. 751–774, ISBN 008167344-7.
6. Groutas, W. C. (1987) Inhibitors of leukocyte elastase and leukocyte cathepsin G. Agents for the treatment of emphysema and related ailments. *Medicinal Research Reviews,* 7(2), 227–241.
7. Heck, H. L., Darby, W. L., Bhown, A., Miller, E. J., Bennet, J. C. (1985) Isolation, characterization, and amino terminal amino acid sequence of human leukocyte elastase from normal donors. *Analytical Biochemistry,* 149, 153–162.
8. Jackson, A. H., Hill, S. L., Afford, S. C., Stockley, R. A. (1984) Sputum soluble phase proteins and elastase activity in patients with cystic fibrosis. *J. Respir. Dis.* 65, 114–124.
9. Metcalf, J. A., Gallin, J. I., Nauseef, W. M., Root, R. K. (1986) *Laboratory Manual of Neutrophil Function,* Raven Press Ltd., New York.
10. Shephard, E. G., Anderson, R., Rosen, O., Myer, M. S., Fridkin, M., Strachan, A. F. & De Beer, F. C. (1990) Peptides generated from C-reactive protein by a neutrophil membrane protease. Amino acid sequence and effects of peptides on neutrophil oxidative metabolism and chemotaxis. *J. Immunol.,* 145, 1469–1476.
11. Shephard, E. G., Kelly, S. L., Anderson, R. & Fridkin, M. (1992) Characterization of neutrophil-mediated degradation of human C-reactive protein and identification of the protease. *Clin. Exp. Immunol.,* 87, 509–513.
12. Vachino, G., Heck, L. W., Gelfand, J. A., Kaplan, M. M., Burke, J. F., Berninger, R. W., McAdam, K. P. (1988) Inhibition of human neutrophil and *Pseudomonas* elastases by the amyloid P-component: A constituent of elastic fibers and amyloid deposits. *J. Leukocyte Biol.* 44, 529–534.
13. Yavin, E. J., Rosen, O., Pontet, M., Shephard, E. G., Fridkin, M. (1995) Proteolysis of human C-reactive protein by neutrophil-derived lysosomal enzymes generates peptides which modulate neutrophil function: Implication to the anti-inflammatory mechanism. *Letters in Peptide Science,* 2, 7–16.
14. Yavin, E. J., Yan, L., Desiderio, D. M. and Fridkin, M. (1996) Synthetic peptides derived from the sequence of human C-reactive protein inhibit the enzymatic activities of human leukocyte elastase and human leukocyte cathepsin G. *Int. J. Peptide Protein Res.,* 48,465–476.
15. Yavin, E. J., Eisenstein, M. and Fridkin, M. (1997) Binding pockets on the surface of human leukocyte elastase and human leukocyte cathepsin G. Implications to the design of inhibitors derived from human C-reactive protein. *Biomed. Pep. Prot. Nucleic acids*, In press.

The invention claimed is:

1. A method for inhibiting the enzymatic activity of human Leukocyte Elastase (hLE) and/or human Cathepsen G (hCG), in a patient having tissue damage caused by the enzymatic activity of hLE and/or hCG, comprising administering to the patient an effective amount of a peptide capable of inhibiting in vitro the enzymatic activity of hLE and/or of hCG, said administration being such that said peptide comes into contact with said hLE and/or hCG, wherein said peptide is a core peptide of the formula:

$Glu_{62}$-Ile-Leu-Ile-Phe-Trp-Ser-Lys-Asp-Ile$_{71}$ (residues 62–71 of SEQ ID NO:1).

* * * * *

SEQUENCE LISTING

<160> NUMBER OF SEQ ID NOS: 12

<210> SEQ ID NO 1
<211> LENGTH: 206
<212> TYPE: PRT
<213> ORGANISM: Homo sapiens

<400> SEQUENCE: 1

```
Glu Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
    50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
            100                 105                 110

Gly Lys Pro Arg Val Arg Lys Ser Leu Lys Lys Gly Tyr Thr Val Gly
        115                 120                 125

Ala Glu Ala Ser Ile Ile Leu Gly Gln Glu Gln Asp Ser Phe Gly Gly
    130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
        195                 200                 205
```

<210> SEQ ID NO 2
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: The N-terminal Ala residue is modified with a
      methoxysuccinyl moiety and the C-terminal Val residue is modified
      with a nitroanilide moiety.

<400> SEQUENCE: 2

Ala Ala Pro Val
1

<210> SEQ ID NO 3
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: The N-terminal Ala residue is modified with a succinyl moiety and the C-terminal Phe residue is modified with a
nitroanilide moiety.

<400> SEQUENCE: 3

Ala Ala Pro Phe
1

<210> SEQ ID NO 4
<211> LENGTH: 15
<212> TYPE: PRT
<213> ORGANISM: Artificial Sequence
<220> FEATURE:
<223> OTHER INFORMATION: synthetic

<400> SEQUENCE: 4

Asp Ile Leu Ile Phe Trp Ser Lys Asp Ile Gly Tyr Ser Phe Thr
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: synthetic

<400> SEQUENCE: 5

Glu Ile Leu Ile Phe Trp Pro Lys Asp Ile Gly Tyr Ser Phe Thr
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa is Ornithine

<400> SEQUENCE: 6

Glu Ile Leu Ile Phe Trp Ser Xaa Asp Ile Gly Tyr Ser Phe Thr
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa is 2,4-diaminobutyric acid

<400> SEQUENCE: 7

Glu Ile Leu Ile Phe Trp Ser Xaa Asp Ile Gly Tyr Ser Phe Thr
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: synthetic

<400> SEQUENCE: 8

Glu Ile Leu Ile Phe Trp Ser Lys Ala Ile Gly Tyr Ser Phe Thr

```
<210> SEQ ID NO 9
<211> LENGTH: 15
<212> TYPE: PRT
<213> ORGANISM: Artificial Sequence
<220> FEATURE:
<223> OTHER INFORMATION: synthetic

<400> SEQUENCE: 9

Glu Ile Leu Ile Phe Trp Ser Lys Glu Ile Gly Tyr Ser Phe Thr
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: synthetic

<400> SEQUENCE: 10

Thr Phe Ser Tyr Gly Ile Asp Lys Ser Trp Phe Ile Leu Ile Glu
1               5                   10                  15

<210> SEQ ID NO 11
<211> LENGTH: 10
<212> TYPE: PRT
<213> ORGANISM: Artificial Sequence
<220> FEATURE:
<223> OTHER INFORMATION: synthetic

<400> SEQUENCE: 11

Glu Ile Leu Ile Phe Trp Ser Ala Asp Ile
1               5                   10

<210> SEQ ID NO 12
<211> LENGTH: 10
<212> TYPE: PRT
<213> ORGANISM: Artificial Sequence
<220> FEATURE:
<223> OTHER INFORMATION: synthetic

<400> SEQUENCE: 12

Glu Ile Leu Ile Phe Trp Ser Val Asp Ile
1               5                   10
```